United States Patent
Duncan

(10) Patent No.: US 10,967,024 B2
(45) Date of Patent: Apr. 6, 2021

(54) SYNERGISTIC HERBAL STIMULANT COMPOSITIONS

(71) Applicant: Aretha Duncan, St. Mary (JM)

(72) Inventor: Aretha Duncan, St. Mary (JM)

( * ) Notice: Subject to any disclaimer, the term of this patent is extended or adjusted under 35 U.S.C. 154(b) by 159 days.

(21) Appl. No.: 16/142,872

(22) Filed: Sep. 26, 2018

(65) Prior Publication Data

US 2020/0093878 A1 Mar. 26, 2020

(51) Int. Cl.
| | |
|---|---|
| *A61K 36/296* | (2006.01) |
| *A61K 36/41* | (2006.01) |
| *A61K 36/25* | (2006.01) |
| *A61K 36/48* | (2006.01) |
| *A61K 36/81* | (2006.01) |
| *A61K 36/31* | (2006.01) |
| *A61K 36/88* | (2006.01) |
| *A61K 36/185* | (2006.01) |

(52) U.S. Cl.
CPC .......... *A61K 36/296* (2013.01); *A61K 36/185* (2013.01); *A61K 36/25* (2013.01); *A61K 36/31* (2013.01); *A61K 36/41* (2013.01); *A61K 36/48* (2013.01); *A61K 36/81* (2013.01); *A61K 36/88* (2013.01)

(58) Field of Classification Search
None
See application file for complete search history.

(56) References Cited

U.S. PATENT DOCUMENTS

| | | | |
|---|---|---|---|
| 8,197,867 B1 | 6/2012 | Blackford | |
| 8,968,799 B2 | 3/2015 | Beggan | |
| 9,839,651 B1 | 12/2017 | Vakina et al. | |
| 2002/0127285 A1 | 9/2002 | Xiu | |
| 2003/0008048 A1 | 1/2003 | Winston et al. | |
| 2006/0222682 A1* | 10/2006 | Andrews ............... | A61K 36/185 424/439 |
| 2007/0116786 A1 | 5/2007 | Zheng et al. | |
| 2008/0102139 A1 | 5/2008 | Baez Acosta | |
| 2009/0098230 A1 | 4/2009 | Andrews | |
| 2009/0110674 A1 | 4/2009 | Loizou | |
| 2016/0206673 A1* | 7/2016 | Miller .................... | A61K 36/23 |
| 2018/0110818 A1 | 4/2018 | Komorowski et al. | |

FOREIGN PATENT DOCUMENTS

| | | | |
|---|---|---|---|
| IN | 201100550 I1 | * | 4/2011 |
| RU | 2114628 C1 | * | 3/1997 |

OTHER PUBLICATIONS

Darbinyan et al., Rhodiola rosea in stress induced fatigue—A double bind cross-over study of a standardized extract SHR-5 with a repeated low-dose regimen on the mental performance of healthy physicians during night duty, 2000, Phytomedicine, 7: 365-371.*
Medicalnewstoday2017, https://www.medicalnewstoday.com/articles/319084.*
Gonzales et al., Effect of Lepidium meyenii (Maca), a root with aphrodisiac and fertility-enhancing properties, on serum reproductive hormone levels in adult healthy men, 2003, J Endocrinology, 176: 163-168.*
Hsueh et al., Herb-Drug Interaction of Epimedium sagittatum (Sieb. etZucc.) Maxim Extract on the Pharmacokinetics of Sildenafil in Rats, 2013, Molecules, 18: 7323-7335.*
Singh et al., An Overview On Ashwagandha: A Rasayana (Rejuvenator) of Ayurveda, 2011, Afr J Tradit Complement Altern Med, 8: 208-213.*
Tan et al., Antioxidant and antibacterial activity of Rhoeo spathacea (Swartz) Stearn leaves, 2015, J Food Sci Technol, 52: 2394-2400.*

* cited by examiner

*Primary Examiner* — Terry A McKelvey
*Assistant Examiner* — Catheryne Chen
(74) *Attorney, Agent, or Firm* — Thomas J. Germinario

(57) ABSTRACT

A synergistic herbal stimulant composition comprises a mixture, in powdered or extract form, of two or more herbal stimulant ingredients and at least one catalytic herbal ingredient, which effects a synergy between the herbal stimulant ingredients. The herbal stimulant ingredients are preferably selected from the group consisting of Horny Goat Weed (*Epimedium Sagittatum*), Rhodiola Root (*Rhodiola Rosea*), Elueuthero Root (*Eleutherococcus*), Nettle Leaf (*Urticaria Dioica*), Ashwagandha Root (*Withania Somnifera*), Maca Root (*Lepidium Meyenii*), Moringa Root (*Moringa Oleifera*), and Cowitch (*Macuna Pruriens*). The catalytic herbal ingredient is preferably Moses-in-a-basket (*Tradescantia Spathacea*).

3 Claims, No Drawings

SYNERGISTIC HERBAL STIMULANT COMPOSITIONS

FIELD OF INVENTION

The present invention relates generally to the field of herbal compositions and herbal extracts, and more particularly to the field of herbal compositions and herbal extracts which are effective as stimulants.

BACKGROUND OF THE INVENTION

Various herbs and extracts thereof are known to be effective as stimulants that enhance energy levels, libido and physical endurance. While such herbs and herbal extracts have previously been combined in stimulant formulations, the effects of such formulations are merely the sum of the independent contributions of each herbal ingredient. What has been lacking up to this point has been a synergistic herbal stimulant composition, for which the total stimulant effect is greater than the sum of the effects of the separate ingredients.

SUMMARY OF THE INVENTION

The inventors of the present invention have empirically determined that the following herbs have stimulant properties which increase energy levels, libido and physical endurance: Horny Goat Weed (*Epimedium Sagittatum*), Rhodiola Root (*Rhodiola Rosea*), Elueuthero Root (*Eleutherococcus*), Nettle Leaf (*Urticaria Dioica*), Ashwagandha Root (*Withania Somnifera*), Maca Root (*Lepidium Meyenii*), Moringa Root (*Moringa Oleifera*), and Cowitch (*Macuna Pruriens*). While the foregoing herbs and/or extracts thereof can be combined in various stimulant compositions, the inventors' empirical experience indicates that a synergistic effect is not achieved unless a non-stimulant catalytic herbal ingredient is added to the compositions. They have found that the most efficacious synergy-inducing herbal catalyst in the context of herbal stimulant compositions is Moses-in-a-basket (*Tradescantia Spathacea*). Therefore, in its most basic embodiment, the present invention comprises synergistic herbal stimulant compositions containing two or more of the foregoing herbal stimulants, or extracts thereof, combined with the catalytic herb Moses-in-a-basket, or an extract thereof.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENTS

The preferred embodiments of the present invention are synergistic herbal stimulant compositions that are prepared by mixing, in substantially equal portions by weight, multiple selected herbs in powdered form, extracting the powdered herbs in a 10% alcohol solution, and filtering residual powder from the extract.

In the first preferred embodiment, the following selected herbs are used:
1. Horny Goat Weed (*Epimedium Sagittatum*)
2. Rhodiola Root (*Rhodiola Rosea*)
3. Elueuthero Root (*Eleutherococcus*)
4. Nettle Leaf (*Urticaria Dioica*)
5. Ashwagandha Root (*Withania Somnifera*)
6. Maca Root (*Lepidium Meyenii*)
7. Moringa Root (*Moringa Oleifera*)
8. Moses in a basket (*Tradescantia Spathacea*)

In the second preferred embodiment, the following selected herbs are used:
1. Horny Goat Weed (*Epimedium Sagittatum*)
2. Rhodiola Root (*Rhodiola Rosea*)
3. Elueuthero Root (*Eleutherococcus*)
4. Nettle Leaf (*Urticaria Dioica*)
5. Ashwagandha Root (*Withania Somnifera*)
6. Maca Root (*Lepidium Meyenii*)
7. Moringa Root (*Moringa Oleifera*)
8. Cowitch (*Macuna Pruriens*)
9. Moses in a basket (*Tradescantia Spathacea*)

Other embodiments of synergistic herbal stimulants can be prepared by substituting Cowitch for any one of the ingredients in the first preferred embodiment, except Moses-in-a-basket.

Although the preferred embodiments of the present invention have been disclosed for illustrative purposes, those skilled in the art will appreciate that many additions, modifications and substitutions are possible, without departing from the scope and spirit of the present invention as defined by the accompanying claims.

What is claimed is:

1. A synergistic herbal stimulant composition comprising an efficacious combination, in substantially equal proportions by weight, of herbal stimulant ingredients and one synergist herbal ingredient, wherein the herbal stimulant ingredients are Horny Goat Weed (*Epimedium Sagittatum*), Rhodiola Root (*Rhodiola Rosea*), Elueuthero Root (*Eleutherococcus*), Nettle Leaf (*Urticaria Dioica*), Ashwagandha Root (*Withania Somnifera*), Maca Root (*Lepidium Meyenii*) and Moringa Root (*Moringa Oleifera*), and wherein the synergist herbal ingredient is Moses-in-a-basket (*Tradescantia Spathacea*).

2. The synergistic herbal stimulant composition according to claim 1, wherein the herbal stimulant ingredients and the synergist herbal ingredient are extracted in a solvent.

3. A synergistic herbal stimulant composition prepared by a process comprising the steps of:
   (a) mixing, in powdered form and in substantially equal amounts by weight, the herbal stimulant ingredients and the synergist herbal ingredient according to claim 1, so as to produce a powdered herbal mixture;
(b) extracting the powdered herbal mixture in a solvent, so as to produce an extracted herbal mixture; and
(c) filtering residuals of the powdered herbal mixture from the extracted herbal mixture.

\* \* \* \* \*